(12) United States Patent
O'Connor et al.

(10) Patent No.: US 8,535,381 B2
(45) Date of Patent: Sep. 17, 2013

(54) CATALYTIC SURFACE FOR HYDROGEN RELEASE REACTOR

(75) Inventors: David O'Connor, North Bend, WA (US); Robert Nelson, Snoqualamie, WA (US)

(73) Assignee: Asemblon, Inc., Bellevue, WA (US)

( * ) Notice: Subject to any disclaimer, the term of this patent is extended or adjusted under 35 U.S.C. 154(b) by 1190 days.

(21) Appl. No.: 12/243,519

(22) Filed: Oct. 1, 2008

(65) Prior Publication Data
US 2009/0093886 A1    Apr. 9, 2009

Related U.S. Application Data

(60) Provisional application No. 60/978,297, filed on Oct. 8, 2007.

(51) Int. Cl.
*A61F 2/30*    (2006.01)
*D02G 3/02*    (2006.01)
*D03D 15/00*   (2006.01)
*B05D 3/02*    (2006.01)

(52) U.S. Cl.
USPC ...... 623/18.11; 428/367; 442/229; 427/383.3

(58) Field of Classification Search
None
See application file for complete search history.

(56) References Cited

U.S. PATENT DOCUMENTS

| | | | | |
|---|---|---|---|---|
| 4,816,124 | A  * | 3/1989 | Manabe et al. | 204/192.14 |
| 2004/0040416 | A1* | 3/2004 | Erlebacher et al. | 75/345 |
| 2007/0048521 | A1* | 3/2007 | Istvan | 428/367 |

* cited by examiner

*Primary Examiner* — Suzanne Ziska
*Assistant Examiner* — Thurman Wheeler
(74) *Attorney, Agent, or Firm* — Olympic Patent Works PLLC

(57) ABSTRACT

There is disclosed a gold surface for the catalytic release of hydrogen from an alkane thiol. More specifically, the present disclosure provides a large surface area of gold on a carbon fiber scaffold that does not contain any sublayers of metals that can block the catalytic release of hydrogen from alkane thiols or form other reactions that remove the sulfur moiety from alkane thiol. There is further disclosed a method for forming a gold surface onto woven carbon fiber sheets wherein no sublayer or other intermediate material is used.

5 Claims, No Drawings

CATALYTIC SURFACE FOR HYDROGEN RELEASE REACTOR

CROSS REFERENCE TO RELATED APPLICATION

This patent application claims priority from U.S. provisional patent application 60/978,297 filed 8 Oct. 2007.

TECHNICAL FIELD

The present disclosure provides a gold surface for the catalytic release of hydrogen from an alkane thiol. More specifically, the present disclosure provides a large surface area of gold on a carbon fiber scaffold that does not contain any sublayers of metals that can block the catalytic release of hydrogen from alkane thiols or form other reactions that remove the sulfur moiety from alkane thiol. The present disclosure further provides a method for forming a gold surface onto woven carbon fiber sheets wherein no sublayer or other intermediate material is used.

BACKGROUND

Reactors for hydrogen reformation have been developed to generate hydrogen from various hydrocarbon sources, such as methane, liquefied petroleum gas, liquid motor fuels such a petrol, diesel or methanol/ethanol. This process is generally carried out in two steps. Initially, hydrocarbons and water are converted into hydrocarbon gas and carbon monoxide in an endothermic reaction. This step is also known as a steam reformation process and the reaction takes place at temperatures above 600° C. In a further reaction step, the shift reaction, the carbon monoxide generated in the reforming reaction is converted with water into hydrogen gas and carbon dioxide. This shift reaction occurs at temperatures below 350° C. and is an exothermic reaction.

Hydrogen reformation has also been tried in a membrane reactor design using a process to directly convert hydrocarbons. This process generated hydrogen by converting the hydrocarbon stream in a membrane reactor fitted with a nickel-containing catalyst. WO99/43610, for example, describes a membrane reactor design that contains a hydrogen permeable membrane and a Ni catalyst to generate hydrogen directly from a hydrocarbon (avoiding the carbon monoxide step) through cracking. The hydrocarbon stream is brought into contact with the catalyst at temperatures between 400 and 900° C. so that conversion of the gas takes place, forming hydrogen. Subsequently, the hydrogen selectively permeates the membrane wall and leaves the reactor.

Hydrogen diffusion membranes often are made from palladium-based spiral or a spiral-shaped tube or tube bundle. Alternatively, a palladium alloy on a porous ceramic substrate can function as a hydrogen membrane. The catalyst bed generally consists of a granular bed of catalyst particles or a porous ceramic catalyst material coated with the catalyst. The catalyst bed and the hydrogen diffusion membrane are located in the same reactor vessel and the catalyst bed is often concentrically and coaxially arranged around the hydrogen diffusion membrane.

Reaction control in membrane reactors often requires supply of process heat into the reactor in order to carry out an endothermic reaction, such as the dehydrogenation of an alkane thiol into its corresponding thiophene.

Catalysts for chemical reactions are generally metals or metal oxides and often made from mixtures of metals called "alloys." However, it is difficult to coat metal surfaces onto fibrous bases because of poor adherence and the fact that fibers bend while the metal surface layer does not. This causes flaking off of the metal surface layer and providing exposure of the fiber surface to the chemical milieu or even exposure of a sublayer or "glue-like layer to the chemical milieu where the reaction to be catalyzed is supposed to take place. The result is exposure of the chemical reactants to a mixed surface of desired catalyst, and undesired fiber surface and sublayer surface. The result of exposure to this mixed surface is wrongly catalyzed side reactions or inefficient reactions due to lower surface area of needed catalytic surface. Therefore, there is a need in the art to be able to provide relative continuous catalytic surfaces of the desired metal without exposure to sublayers or underlying fiber surfaces.

Metal coating of carbon fibers and gold in particular has been tried. For example, U.S. Pat. No. 4,606,354 describes a medical implant of a carbon fiber rod having a discontinuous coating for delivering gold ions to the site or an arthritic joint. Specifically this discontinuous gold fiber implant was made with nickel-coated carbon fibers because the group was unable to provide even a discontinuous coating on carbon fibers without a sublayer of another metal. Therefore, a discontinuous gold coating having a significant nickel surface would cause Ni-catalyzed reactions in addition to Au-catalyzed reactions and this resulting surface would be undesirable for a reactor module where side reactions (such as those catalyzed by Ni or a desulfurization nature) would be undesirable.

U.S. Pat. No. 4,816,124 describes metal coating a series of fibers (including carbon fibers) with metals, including gold. However, the metal coated fibers are for shielding and are not designed to operate at temperatures of reactor modules (such as above 200° C.) because the process requires the initial application of base coating resins in order to apply the metals and the base coating resins applied would not be able to operate at the elevated temperatures of a catalytic reactor module.

Catalytic surfaces must be made such that the catalyst does not get poisoned and to keep the reaction being catalyzed from forming unwanted side reactions. In the case of an alkane thiol, for example, much catalytic work has been done to try to desulfurize the molecule into a linear alkane or even a partially dehydrogenated alkene. Earlier characterization (Ratner and Naeemi, U.S. Pat. No. 7,186,396 (the disclosure of which is incorporated by reference herein) describe a gold catalyzed thiol that forms a thiophene and the release of three moles of hydrogen per mole of alkane thiol. Yet that reaction was conducted in a static or laboratory setting, not in a flow-through or dynamic environment. Therefore, there is a need in the art to design and build reaction modules capable of dehydrogenating an alkane thiol into a thiophene without side reactions of other desulfurized alkanes or alkenes. The present invention was made to design an appropriate catalytic surface to address this need.

SUMMARY

The present disclosure provides a surface for catalytic hydrogen release comprising a carbon fiber base and a gold surface with the proviso that there is no sublayer or presence of any other metal surface. Preferably, the carbon fibers have an average diameter of from about 1.0 to about 10.0 microns. Preferably, the carbon fibers are woven into a cloth-like matrix having an open area of from about 10% to about 40% of the total surface. Preferably, the gold surface has a thickness of from about 0.1 to about 0.125 microns.

The present disclosure provides a method for applying a gold surface to a woven carbon fiber base, comprising:

(a) providing a sheet of woven carbon fiber submerged within an aqueous solvent having a surface;

(b) floating a sheet of gold foil on the surface of the aqueous solvent;

(c) lifting the woven carbon fiber sheet out of the aqueous solvent so that it aligns with the floating gold foil and forms a surface on the woven carbon fiber sheet; and (d) baking the woven carbon fiber sheet having a gold foil surface at a temperature of from about 100° C. to about 150° C. for at least one hour.

Preferably, the carbon fibers in the woven sheet have an average diameter of from about 1.0 to about 10.0 microns. Preferably, the woven carbon fibers have an open area of from about 10% to about 40% of the total surface. Preferably, the gold foil has a thickness of from about 0.1 to about 0.125 microns. Preferably, the aqueous solvent is selected from the group consisting of water, methanol, ethanol, propanol (and isopropanol), DMF, and mixtures thereof.

The present invention further provides a method for treating an arthritic joint, comprising administering an implant into the joint synovial cavity, wherein the implant comprises a carbon fiber base and a gold surface with the proviso that there is no sublayer or presence of any other metal surface. Preferably, the carbon fibers have an average diameter of from about 1.0 to about 10.0 microns. Preferably, the carbon fibers are woven into a cloth-like matrix having an open area of from about 10% to about 40% of the total surface. Preferably, the gold surface has a thickness of from about 0.1 to about 0.125 microns.

DETAILED DESCRIPTION

The present disclosure provides a gold surface on carbon fiber that has no sublayer or other intermediate binding layer to help adhere the gold to the carbon fiber. The references that "metalized" carbon fiber or put various metals (including gold) onto carbon fiber structures provided a sublayer or other intermediate layer between the gold and the carbon fibers.

Thiol-Based Conversion with Gold Surface

For the application of an alkane thiol conversion to its corresponding thiophene, a gold surface catalyst is used. Pure gold or gold alloys are made into sheets that are exquisitely thin, know as gold leaf. One such manufacturer is Fabbriche Riunite Metalli in Italy. However, such gold sheets are delicate and difficult to handle. Therefore the challenge is to figure out how to put such extremely thin gold sheets onto carbon fiber surfaces and particular carbon fiber woven into a cloth-like matrix without underlying adhesive precursors or other sublayers. Such resin or metal sublayers, if exposed as part of a catalytic surface, can catalyze inappropriate reactions (such as a desulfurization of alkane thiol) that would cause a hydrogen storage system to not function. The process of the present disclosure is primarily a mechanical process, not a chemical process, with the challenge being to avoid breaking the very think gold sheets yet providing a continuous (not a discontinuous) surface to woven carbon fiber sheets.

Dry, woven, non-impregnated carbon fiber cloth was used (1) because it is a strong mechanical support for the final gold surface, (2) because it is a good heat conductor, (3) because it is chemically inert and will not act as a catalyst to catalyze any undesirable desulfurization reactions of an alkane thiol, and (4) because a carbon fiber cloth can withstand relatively high temperatures.

The first step of the process is to place the carbon fiber cloth in the bottom of a bath of aqueous solution (preferably water with or without a short chain alcohol). The side to have the gold leaf attached is oriented upward, or toward the aqueous solvent surface. The depth of the aqueous solvent is sufficient so as to allow a gap between the carbon fiber sheet and the top of the aqueous solvent. A gold leaf is floated on the top of the aqueous solvent and if there is a backing to the gold leave (likely) that backing material is slid off and the gold leaf will float without such support on the surface of the aqueous solvent. Preferably, the gold leaf sheet is inserted vertically into the aqueous solvent solution and the backing material separates the backing from the metal. The carbon fiber cloth is then raised up horizontally under the floating gold sheet so that the surfaces are aligned. It is preferred that the surface area of the carbon fiber sheet is at least as large (in the length and width dimensions) as the surface are of the gold sheet. During this attachment process, excess aqueous solvent is drained through the carbon fiber woven mesh. At this point, the carbon fiber sheet having the gold surface can have the gold re-flated in the aqueous solvent to re-set or re-orientate the gold surface on the carbon fiber sheet. However, after exposing the carbon fiber and gold in a dry oven, the process cannot be reversed.

The carbon and gold sheet is "set" by baking in an oven for at least one hour at a temperature of at least 100° C. and preferably at least 120° C. for at least one hour and more preferably overnight. This removes any residual aqueous solvent from the product and allows for stacking of such gold-on-woven carbon fiber sheets to be placed in a reactor.

Arthritis Implant

The present disclosure further provides a method for treating an arthritic joint, comprising administering an implant into the joint synovial cavity, wherein the implant comprises a carbon fiber base and a gold surface with the proviso that there is no sublayer or presence of any other metal surface. Preferably, the carbon fibers have an average diameter of from about 1.0 to about 10.0 microns. Preferably, the carbon fibers are woven into a cloth-like matrix having an open area of from about 10% to about 40% of the total surface. Preferably, the gold surface has a thickness of from about 0.1 to about 0.125 microns.

Specifically, the gold surface and absence of any toxic binding agents or sublayers provides a continuous release of gold ions regulated by the electrolyte composition of the synovial fluid contained within the diseased joint. Moreover, as an arthritic joint tends to have episodes of inflammatory activity, such episodes often reflect changes in the electrolytic composition of the synovial fluid in the diseased joint to provide for a higher release rate of gold ions during periods of inflammatory activity. The rate of ion release is provided to measuring ion release rates with differing pH of the solution bathing the implanted device. As episodes of inflammatory activity tend to have more acid pH, the data should show release rates increasing as a function of decreasing pH.

We claim:

1. A method for applying a gold surface to a woven carbon fiber base, comprising:

(a) providing a sheet of woven carbon fiber submerged within an aqueous solvent having a surface;

(b) floating a sheet of gold foil on the surface of the aqueous solvent;

(c) lifting the woven carbon fiber sheet out of the aqueous solvent so that it aligns with the floating gold foil and forms a surface on the woven carbon fiber sheet; and (d) baking the woven carbon fiber sheet having a gold foil surface at a temperature of from about 100° C. to about 150° C. for at least one hour.

2. The method for applying a gold surface to a woven carbon fiber base of claim 1, wherein the carbon fibers in the woven sheet have an average diameter of from about 1.0 to about 10 microns.

3. The method for applying a gold surface to a woven carbon fiber base of claim 1, wherein the woven carbon fibers have an open area of from about 10% to about 40% of the total surface.

4. The method for applying a gold surface to a woven carbon fiber base of claim 1, wherein the gold foil has a thickness of from about 0.1 to about 0.125 microns.

5. The method for applying a gold surface to a woven carbon fiber base of claim 1, wherein the aqueous solvent is selected from the group consisting of water, methanol, ethanol, propanol, isopropanol, DMF, and mixtures thereof.

* * * * *